United States Patent
Shinohara et al.

(10) Patent No.: US 10,629,325 B2
(45) Date of Patent: Apr. 21, 2020

(54) SILVER CHLORIDE PASTE

(71) Applicant: TATSUTA ELECTRIC WIRE & CABLE CO., LTD., Osaka (JP)

(72) Inventors: Keisho Shinohara, Kyoto (JP); Takashi Morita, Kyoto (JP); Shinji Yoshino, Kyoto (JP); Tsunehiko Terada, Kyoto (JP); Akio Takahashi, Kyoto (JP)

(73) Assignee: TATSUTA ELECTRIC WIRE & CABLE CO., LTD., Osaka (JP)

( * ) Notice: Subject to any disclaimer, the term of this patent is extended or adjusted under 35 U.S.C. 154(b) by 0 days.

(21) Appl. No.: 16/309,729

(22) PCT Filed: Jun. 23, 2017

(86) PCT No.: PCT/JP2017/023234
§ 371 (c)(1),
(2) Date: Dec. 13, 2018

(87) PCT Pub. No.: WO2018/003702
PCT Pub. Date: Jan. 4, 2018

(65) Prior Publication Data
US 2019/0139670 A1    May 9, 2019

(30) Foreign Application Priority Data
Jun. 30, 2016   (JP) .................. 2016-130502

(51) Int. Cl.
*H01B 1/00* (2006.01)
*A61B 5/00* (2006.01)
*H01B 1/22* (2006.01)
*A61B 5/0408* (2006.01)

(52) U.S. Cl.
CPC ............. *H01B 1/22* (2013.01); *A61B 5/0408* (2013.01)

(58) Field of Classification Search
CPC ... H01B 1/00; H01B 1/02; H01B 1/06; H01B 1/22
See application file for complete search history.

(56) References Cited

U.S. PATENT DOCUMENTS 4,270,543 A * 6/1981 Tabuchi ............... A61B 5/0408
                                                      600/396
5,565,143 A * 10/1996 Chan ...................... H01B 1/20
                                                      252/514
(Continued)

FOREIGN PATENT DOCUMENTS

EP        2000173 A2    12/2008
JP       51026789 A     3/1976
(Continued)

OTHER PUBLICATIONS

International Search Report dated Sep. 12, 2017 filed in PCT/JP2017/023234.
(Continued)

*Primary Examiner* — Mark Kopec
(74) *Attorney, Agent, or Firm* — Rankin, Hill & Clark LLP

(57) ABSTRACT

A silver chloride paste contains: a binder resin; and supported silver chloride that includes (i) a support and (ii) silver chloride supported on the support. The binder resin is, for example, a polyester resin. The support is, for example, silica.

4 Claims, 2 Drawing Sheets

(56) References Cited

U.S. PATENT DOCUMENTS

| | | | |
|---|---|---|---|
| 5,851,438 A * | 12/1998 | Chan | A61N 1/0436 252/514 |
| 2001/0031988 A1 | 10/2001 | Kurata | |
| 2003/0051799 A1 * | 3/2003 | Stevenson | B29C 41/06 156/230 |
| 2014/0081118 A1 * | 3/2014 | Reinhold, Jr. | A61B 5/0404 600/384 |
| 2018/0215941 A1 * | 8/2018 | Hagar | C09D 5/12 |

FOREIGN PATENT DOCUMENTS

| | | | |
|---|---|---|---|
| JP | 63-19870 A | | 2/1978 |
| JP | 57021302 U1 | | 2/1982 |
| JP | 58007227 A | | 1/1983 |
| JP | 59190649 A | | 10/1984 |
| JP | 401010164 A | * | 1/1989 |
| JP | H05095922 A | | 4/1993 |
| JP | 05176904 A | | 7/1993 |
| JP | 05182513 A | | 7/1993 |
| JP | 2001292972 A | | 10/2001 |
| JP | 2007085763 A | | 4/2007 |
| JP | 2014517759 A | | 7/2014 |
| JP | 2015210883 A | | 11/2015 |
| JP | 02018168445 A | * | 11/2018 |
| WO | 2001004614 A1 | | 1/2001 |
| WO | 2007111368 A1 | | 10/2007 |
| WO | 2015162931 A1 | | 10/2015 |

OTHER PUBLICATIONS

International Preliminary Report on Patentability dated Jan. 10, 2019 filed in PCT/JP2017/023234.

T. Endo et al. "Preparation and Catalytic Activities of Noble Metal Binary Particle Dendrimer Nanocomposites", Journal of the Japan Society of Colour Material, 2005, pp. 185-190, vol. 78, No. 4, Japan Society of Colour Material, Japan; Partial translation.

International Search Report dated Aug. 8, 2017 filed in PCT/JP2017/023228.

International Preliminary Report on Patentability dated Jan. 10, 2019 filed in PCT/JP2017/023228.

International Preliminary Report on Patentability dated Jan. 10, 2019 filed in PCT/JP2017/023226.

International Search Report dated Sep. 26, 2017 filed in PCT/JP2017/023226.

Mert Tuncer, "Effects of Chloride Ion and the Types of Oxides on the Antibacterial Activities of Inorganic Oxide Supported AG Materials", July 2007, Izmir Institute of Technology, total 79 pages.; Cited in US Office Action.

US Office Action dated Jan. 10, 2020 issued in U.S. Appl. No. 16/311,444.

* cited by examiner

SILVER CHLORIDE PASTE

TECHNICAL FIELD

The present invention relates to a silver chloride paste.

BACKGROUND ART

Patent Literature 1 discloses a bioelectrode including a nonpolarizable electrode containing silver/silver chloride. The nonpolarizable electrode containing silver/silver chloride disclosed in Patent Literature 1 is formed from a silver/silver chloride paste.

CITATION LIST

Patent Literature

[Patent Literature 1]
Japanese Patent Application Publication, Tokukaihei, No. 5-95922
[Patent Literature 2]
Japanese Patent Application Publication, Tokukai, No. 2015-210883
[Patent Literature 3]
PCT International Publication No. WO2015/162931

SUMMARY OF INVENTION

Technical Problem

An object of the present invention is to provide a silver chloride paste that has nonpolarizable properties and that has a novel configuration.

Solution to Problem

In order to attain the above object, a subject matter in accordance with Aspect 1 of the present invention is a silver chloride paste including: a binder resin; and supported silver chloride that includes (i) a support and (ii) silver chloride supported on the support.

This makes it possible to obtain a silver chloride paste that has nonpolarizable properties and that has a novel configuration.

DESCRIPTION OF EMBODIMENTS

[1] Silver Chloride Paste

A silver chloride paste according to one or more embodiments of the present invention includes: a binder resin; and supported silver chloride including (i) a support and (ii) silver chloride supported on the support.

A silver chloride paste according to one or more embodiments of the present invention is a silver chloride paste that has nonpolarizable properties and that has a novel configuration. Thus, the silver chloride paste according to one or more embodiments of the present invention is a silver chloride paste suitable for formation of a nonpolarizable electrode of a bioelectrode, a reference electrode, or the like.

[2] Binder Resin

The binder resin is, for example, a thermoplastic resin. Specific examples of the binder resin include polyester resins, polyurethane resins, acrylic resins, alkyd resins, phenoxy resins, butyral resins, and polyvinylalcohol resins. Examples of polyester resins include: solvent-soluble-type polyesters TP-220, TP-217, TP-249, TP-235, TP-236, TP-290, TP-270, LP-035, LP-033, LP-050, LP-011, LP-022, and TP-219 available from The Nippon Synthetic Chemical Industry Co., Ltd.; elitel resins UE3220, UE3223, UE3230, UE3231, UE3400, UE3500, UE3200, UE9200, UE3201, UE3203, UE3600, UE9600, UE3660, UE3690, UE3210, UE3215, UE3216, UE3620, UE3240, and UE3250 available from UNITIKA LTD.; and ARON MELT PES310S30 and PES360HVXM30 available from TOAGOSEI CO., LTD.

[3] Supported Silver Chloride

The supported silver chloride includes: a support; and silver chloride supported on the support.

[3.1] Support

A material for the support can be any of various materials such as metals (preferably other than silver), nonmetals, organic substances, and inorganic substances. In order for the supported silver chloride to be readily dispersed in the binder resin, it is preferable to prevent the supported silver chloride from precipitating in the binder resin. To achieve this, the support is preferably one that is equal or close in density to the binder resin. Furthermore, the support is preferably a low-cost support on which silver chloride can be easily supported.

Specifically, the support can be (1) an acrylic resin, a polyurethane resin, a polyester resin, or a polyamide resin; (2) polymer particles composed of an epoxy resin or the like, silica beads, mica beads, or glass beads, or (3) inorganic particles composed of calcium carbonate or the like.

[3.2] Example 1 of Supported Silver Chloride

Example 1 of the supported silver chloride is silica-supported silver chloride, which is constituted by: silica (silicon dioxide): and silver chloride supported on the silica.

The silica which supports silver chloride may be wet-process silica such as precipitated silica or gelation method silica (gel method silica), or may be dry-process silica. The silica is preferably gelation method silica. In this embodiment, the silica is gelation method silica.

Figure 1:
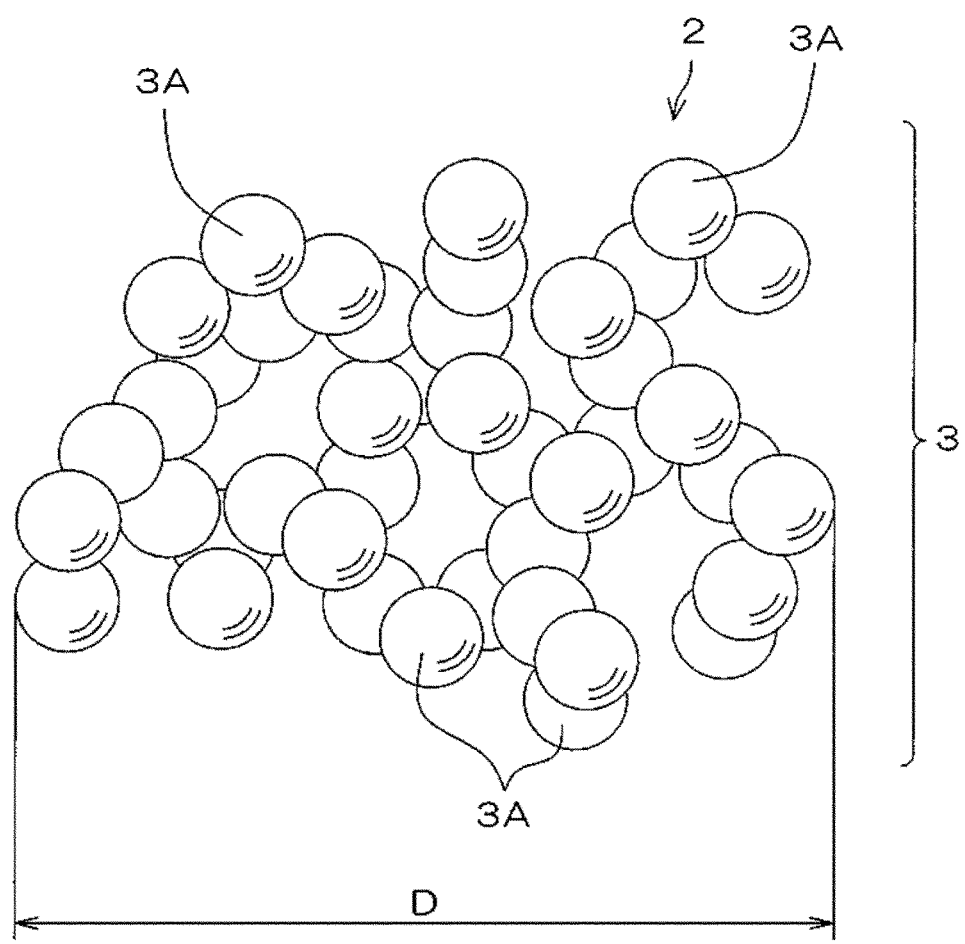
FIG. 1 schematically illustrates one example of a particulate structure of silica constituted by gelation method silica.

FIG. 1 schematically illustrates one example of a particulate structure of silica constituted by gelation method silica. Silica 2, which is constituted by gelation method silica, has a particulate structure such that, for example, a plurality of primary particles (skeleton grains) 3A are grouped in the form of a bunch of grapes to form a secondary particle 3.

In the following descriptions, the specific surface area of silica refers to surface area per unit mass. The surface area of silica is the sum of the external surface area and the internal surface area (i.e., the surface area of the walls of pores in the silica) of silica. The pore volume of silica refers to the volume of pores in silica per unit mass. The mean pore size of silica refers to the mean of the diameters of the pores (cavities) in silica. The mean particle size of silica refers to the mean of diameters D (see FIG. 1) of secondary particles.

The specific surface area of the silica is preferably not less than 20 $m^2/g$ and not more than 1000 $m^2/g$, particularly preferably not less than 100 $m^2/g$ and not more than 700 $m^2/g$. The pore volume of the silica is preferably not less than 0.2 ml/g and not more than 2.0 ml/g, particularly preferably not less than 0.3 ml/g and not more than 1.2 ml/g. The mean pore size of the silica is preferably not less than 2 nm and not greater than 100 nm, particularly preferably not less than 2 nm and not greater than 30 nm. The mean particle size of the silica is preferably not less than 1 μm and not greater than 50 μm, particularly preferably not less than 2 μm and not greater than 30 μm.

Figure 2:
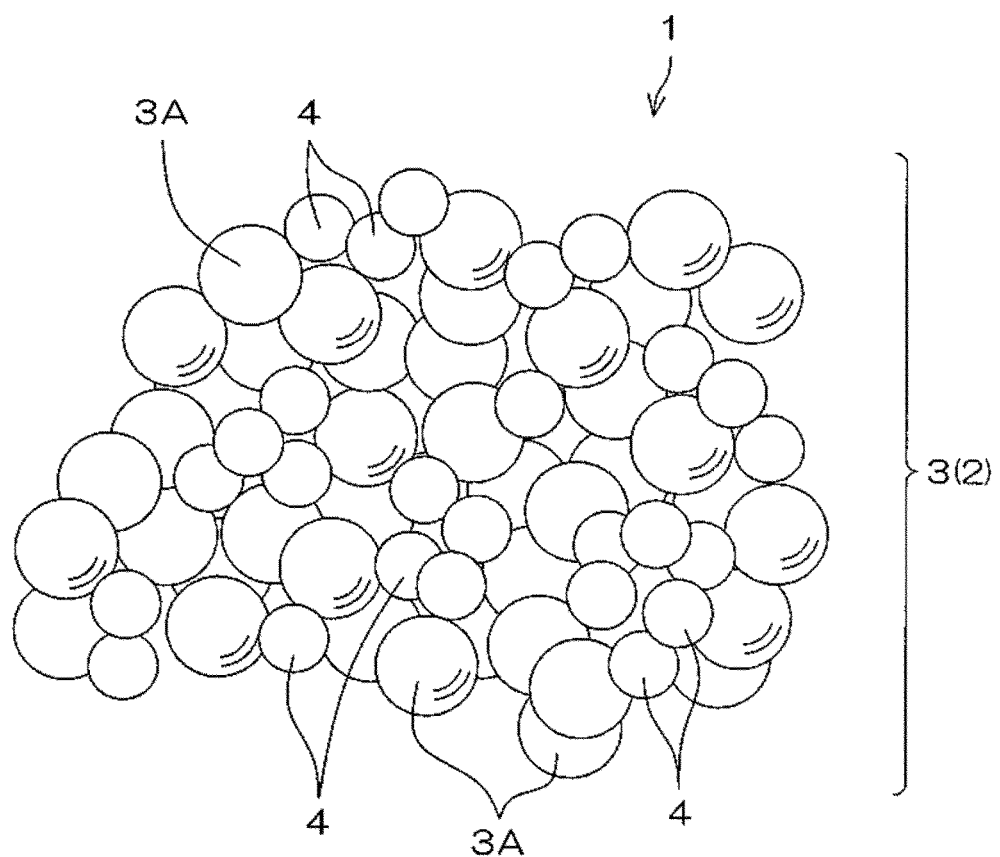
FIG. 2 schematically illustrates one example of a particulate structure of silica-supported silver chloride which is constituted by: silica constituted by gelation method silica; and silver chloride supported on the silica.

FIG. 2 schematically illustrates one example of a particulate structure of silica-supported silver chloride which is constituted by: silica constituted by gelation method silica; and silver chloride supported on the silica. Silica-supported silver chloride 1 illustrated in FIG. 2 includes: the silica 2; and silver chloride 4 supported on the surface (including the walls of pores) of the silica 2.

The silica-supported silver chloride is produced by, for example, a production method discussed below. The production method includes the steps of: producing a silver compound solution by dissolving a silver compound in a solvent; and allowing the silver compound to be supported on the silica (including the walls of pores) with the use of the silver compound solution. The silver compound used here is silver nitrate, silver chloride, or the like.

For example, in a case where the silver compound is silver nitrate, a silver nitrate solution is first produced by dissolving silver nitrate powder in an aqueous solvent. Next, the silver nitrate solution is used to allow silver nitrate to be supported on silica. A method used to allow silver nitrate to be supported on silica is, for example, precipitation, gelatinization, impregnation, ion exchange, or the like method. Then, the silver nitrate supported on silica is allowed to react with a chloride-ion-containing compound such as hydrochloric acid or sodium chloride, and thereby silver chloride is supported on the silica.

For example, in a case where the silver compound is silver chloride, a silver chloride solution is first produced by dissolving silver chloride powder in an aqueous solution such as ammonia water, a concentrated hydrochloric acid solution, an aqueous alkaline cyanide solution, an aqueous thiosulfate solution, or an aqueous ammonium carbonate solution. Next, the silver chloride solution is used to allow silver chloride to be supported on silica. A method used to allow silver chloride to be supported on silica is, for example, precipitation, gelatinization, impregnation, ion exchange, or the like method. Then, an organic solvent that dissolves in an aqueous solvent, such as methanol, ethanol, isopropyl alcohol, methyl cellosolve, or butyl cellosolve, is added to the silver chloride supported on silica, and thereby the silver chloride is supported on silica.

[3.2.1] Example 1 of Silica-Supported Silver Chloride

Example 1 of silica-supported silver chloride includes: silica which is constituted by gelation method silica (SYLYSIA710 (trade name) available from FUJI SILYSIA CHEMICAL LTD.); and silver chloride (AgCl) supported on the silica. The silica (silicon dioxide) content of the silica-supported silver chloride of Example 1 is 61 wt %, and the silver chloride content of the silica-supported silver chloride is 39 wt %. In Example 1, the specific surface area of the silica is 397 $m^2/g$, and the mean particle size of the silica is 2.9 μm.

The following description discusses a method of producing Example 1 of silica-supported silver chloride. First, 40 g of silver nitrate powder was dissolved in 50 ml of ion-exchanged water to prepare a silver nitrate solution. Next, 20 g of silica (SYLYSIA710 (trade name) available from FUJI SILYSIA CHEMICAL LTD.) was added to the silver nitrate solution and stirred for 4 hours. Next, a solid component was collected from the stirred solution with the use of type 5A filter paper, and the collected solid component was dried in a shelf-type dryer at 120° C. for 16 hours. In this way, silica-supported silver nitrate, which is constituted by: silica; and silver nitrate supported on the silica, was obtained.

Next, about 34 g of the silica-supported silver nitrate was added to 200 ml of 1M hydrochloric acid, and stirred for 4 hours. Next, a solid component was collected from the stirred solution with the use of type 5A filter paper, and the collected solid component was washed with 200 ml of ion-exchanged water. Next, the washed solid component was dried in a shelf-type dryer at 120° C. for 16 hours, and then was pulverized. In this way, about 30 g of silica supporting silver chloride (silica-supported silver chloride) was obtained

[3.3] Another Method of Producing Supported Silver Chloride

The supported silver chloride can alternatively be produced by coating silver on a support and then carrying out chlorination. A method of coating silver on a support can be the method disclosed in Patent Literatures 2 and 3 and the like.

[4] Example of Method of Producing Silver Chloride Paste

The following description discusses an example of a method of producing a silver chloride paste in a case where the supported silver chloride is silica-supported silver chloride.

In a vessel with a lid, 50 g powder of silica-supported silver chloride was placed. In the silica-supported silver chloride, the amount of silver chloride supported on silica is any amount falling within the range of not less than 0.1 wt % to 80 wt %.

Next, 25 g of a solvent mixture of methyl ethyl ketone (MEK), ethyl acetate, and toluene (mix ratio: 1:1:1) was added to the vessel, where the solvent was mixed with the powder of silica-supported silver chloride.

Then, 50 g of a binder resin (solvent-soluble-type polyester LP-035 (solid content: 40%) available from The Nippon Synthetic Chemical Industry Co., Ltd.) was added to the vessel and stirred. Specifically, with the use of a stirrer (TK Homodisper MODEL2.5 available from PRIMIX Corporation), stirring was carried out at 3500 r/min for 10 minutes. In this way, a fluidic silver chloride paste with no powder agglomerations was obtained.

Note that the binder resin may be changed from the solvent-soluble-type polyester LP-035 (solid content: 40%) available from The Nippon Synthetic Chemical Industry Co., Ltd. to, for example, elitel No. 3220 (solid content: 40%) available from UNITIKA LTD., elitel No. 9200 (solid content: 40%) available from UNITIKA LTD., or the like.

The stirrer may be some other kind of stirrer, such as a propeller stirrer.

[5] Advantages of Silver Chloride Paste Containing Silica-Supported Silver Chloride The silver chloride paste containing silica-supported silver chloride is advantageous in the following aspects.

Silver chloride agglomerates easily (has low dispersibility), whereas silica does not easily agglomerate (has high dispersibility). Therefore, silica-supported silver chloride is more dispersible and less likely to agglomerate than silver chloride. Because of this, according to the silver chloride paste containing silica-supported silver chloride, silver chloride (silica-supported silver chloride) is less likely to agglomerate.

The silica-supported silver chloride is such that silver chloride is supported on silica (including the walls of pores). This makes it possible to increase the surface area of silver chloride as compared to the conventional silver/silver chloride paste, when the silver chloride paste containing silica-supported silver chloride and the conventional silver/silver chloride paste are equal in the total amount of silver chloride in the paste. This makes it possible to enhance polarization-reducing effect.

The silica-supported silver chloride is such that silver chloride is supported on silica (including the walls of pores). This makes it possible to reduce the amount of silver chloride (or silver) as compared to the conventional silver/silver chloride paste, when the silver chloride paste containing silica-supported silver chloride and the conventional silver/silver chloride paste are to achieve the same total area of exposure of silver chloride within the paste. This makes it possible to provide a less expensive paste.

According to the silver chloride paste containing silica-supported silver chloride, silver chloride supported on the walls of pores (cavities) in the silica does not receive much light. Therefore, the silver chloride paste containing silica-supported silver chloride has improved light resistance as compared to the conventional silver/silver chloride paste which contains silver particles and fine silver chloride particles.

Recap

A silver chloride paste in accordance with Aspect 2 of the present invention is arranged such that, in Aspect 1, in the supported silver chloride, an amount of the silver chloride supported on the support is not more than 80 wt %.

A silver chloride paste in accordance with Aspect 3 of the present invention is arranged such that, in Aspect 1 or 2, an amount of the supported silver chloride in the silver chloride paste is not more than 50 wt %.

A silver chloride paste in accordance with Aspect 4 of the present invention is arranged such that, in any of Aspects 1 to 2, the support is silica.

The present invention can be modified in various manners within the matters described in claims. The present invention is not limited to the embodiments, but can be altered by a skilled person in the art within the scope of the claims. The present invention also encompasses, in its technical scope, any embodiment derived by combining technical means disclosed in differing embodiments.

REFERENCE SIGNS LIST

1 Conductive material
2 Silica
3 Secondary particle
3A Primary particle
4 Silver chloride

The invention claimed is:

1. A silver chloride paste for formation of a bioelectrode, comprising: a binder resin; and supported silver chloride that includes (i) a support and (ii) silver chloride supported on the support,
   wherein the support is silica; and
   a specific surface area of the silica is not less than 20 m$^2$/g and not more than 1000 m$^2$/g.

2. A silver chloride paste for formation of a bioelectrode, comprising: a binder resin; and supported silver chloride that includes (i) a support and (ii) silver chloride supported on the support,
   wherein the support is silica; and
   a pore volume of the silica is not less than 0.2 ml/g and not more than 2.0 ml/g.

3. A silver chloride paste for formation of a bioelectrode, comprising: a binder resin; and supported silver chloride that includes (i) a support and (ii) silver chloride supported on the support,
   wherein the support is silica; and
   a mean pore size of the silica is not less than 2 nm and not greater than 100 nm.

4. A silver chloride paste for formation of a bioelectrode, comprising: a binder resin; and supported silver chloride that includes (i) a support and (ii) silver chloride supported on the support,
   the support is silica; and
   wherein the silica has a particulate structure in which a plurality of primary particles are grouped together to form a secondary particle, and a mean particle size of the silica is not less than 1 μm and not greater than 50 μm, the mean particle size being a mean of diameters of the secondary particles.

* * * * *